United States Patent [19]

Suzuki et al.

[11] 4,296,107
[45] Oct. 20, 1981

[54] MILDIOMYCIN ANALOGS AND A METHOD OF PRODUCTION

[75] Inventors: Takashi Suzuki, Takatsuki; Hidekazu Sawada, Neyagawa; Kazuyoshi Katamoto, Suita, all of Japan

[73] Assignee: Takeda Chemical Industries, Ltd., Osaka, Japan

[21] Appl. No.: 179,555

[22] Filed: Aug. 19, 1980

[30] Foreign Application Priority Data

Aug. 24, 1979 [JP] Japan .................................. 54-108330

[51] Int. Cl.³ ........................ A61K 31/70; C07H 17/00
[52] U.S. Cl. ......................................... 424/180; 536/23
[58] Field of Search ................. 536/23; 424/180, 181, 424/116; 435/85, 87

[56] References Cited

U.S. PATENT DOCUMENTS

4,007,267  2/1977  Kishi et al. ........................... 424/116

OTHER PUBLICATIONS

Chemical Abstracts, vol. 89, 1978, Abstract No. 197860x, Harada, S. et al., "Structure of Mildiomycin, a New Antifungal Nucleoside Antibiotic."

Primary Examiner—Johnnie R. Brown
Assistant Examiner—Blondel Hazel
Attorney, Agent, or Firm—Wenderoth, Lind & Ponack

[57] ABSTRACT

A compound of the formula:

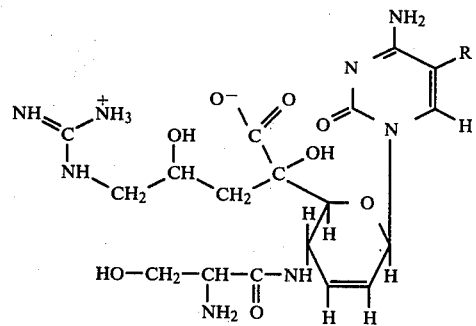

wherein R is hydrogen, a halogen atom or a lower alkyl group, or an acid salt thereof, possesses a superior fungicidal and acaricidal activity suitable for plant uses.

10 Claims, No Drawings

MILDIOMYCIN ANALOGS AND A METHOD OF PRODUCTION

The present invention relates to a compound of the formula:

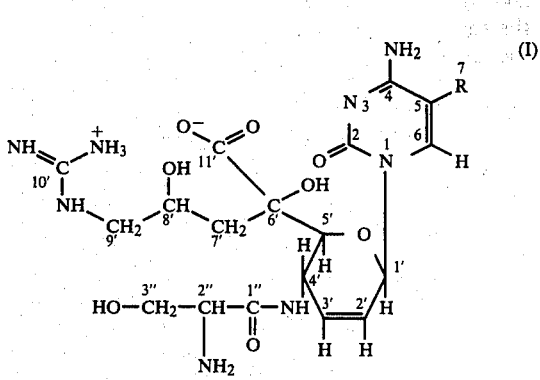

wherein R is hydrogen, a halogen atom or a lower alkyl group, or an acid salt thereof, to a process for producing the same, and to a plant fungicidal and acaricidal agent containing the same.

The present inventors, as the result of extensive research studies, found out that cultivation of a mildiomycin-producing microorganism belonging to the genus Streptoverticillium in a culture medium containing a compound of the formula:

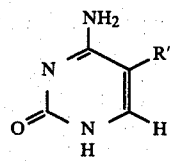

wherein R' is hydrogen, a halogen atom, a lower alkyl or hydroxymethyl group, or an acid salt thereof, affords a compound of the formula:

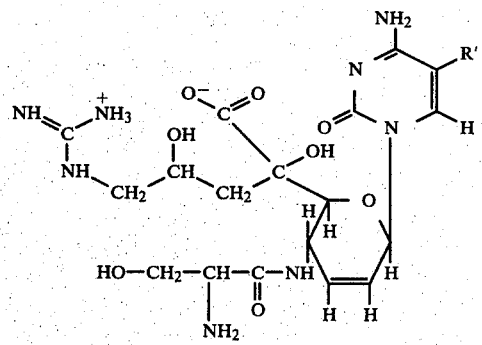

wherein the symbol R' in the formula is as defined hereinbefore, or an acid salt thereof and especially cultivation in a culture medium containing an N-methyl compound in an amount of not less than 3 mM results in favorable production of the compound (II), and that the compound (I) or an acid salt thereof possesses a superior fungicial and acaricidal activity suitable for plant uses, and have completed, on the basis of these findings, the present invention.

In the above formulas, the halogen atoms represented by R and R' include bromine, chlorine, iodine and fluorine. As preferred examples of the alkyl group may be mentioned straight-chain or branched alkyls, and those which are often operable are for example methyl, ethyl, propyl, isopropyl, butyl and isobutyl. The compounds (I) and (III) wherein R and R' are hydrogen atoms can be produced at reduced costs and are favored from a standpoint of commercial production. In addition, the compounds (I) and (III) are utilized as free bases or in the form of acid salts which are prepared according to the conventional methods. As examples of such acid salts, there may be mentioned salts formed with inorganic acids such as hydrochloric acid, sulfuric acid and nitric acid or with organic acids such as formic acid, acetic acid and butyric acid. Salts with hydrochloric acid, sulfuric acid, formic acid, etc., among others, are preferred. The compounds, containing an asymmetric carbon atom, are supposed to assume various configurations, and the compound (I) of the present invention represents the same configuration as mildiomycin as described in Tetrahedron Letters No. 44, pp 4277–4280 (1980).

The mildiomycin-producing microorganisms which are subjected to the production of the compound (III) include strains belonging to Actinomycetes, *Streptoverticillium rimofaciens*, and in particular, IFO 13592 (FERM-P 2549, ATCC 31120) is well-known [The Journal of Antibiotics, vol. 31, no. 6, pp. 511–518, 1978 and U.S. Pat. No. 4,007,267] and one example of the microorganisms that are most effectively employed for the object of conducting into practice the present invention. Such actinomycetes have the common nature of the mycological or physiological properties easily undergoing mutation, and various mutant strains or species are easily obtained, artificially or naturally. Such mutant strains and species, as long as they retain the character to produce the compound (III), can be employed for the object of the present invention.

Production of the compound (III) is conducted by cultivating a mildiomycin-producing microorganism in a culture medium containing a compound (II) or an acid salt thereof. As acid salts of compound (II), may be employed such acid salts as mentioned in the compounds (I), (III). The culture medium which is employable is a medium containing carbon sources, nitrogen sources and inorganic salts generally assimilable by microorganisms, and materials being effective in trace amounts such as trace nutrients and growth promoters, if necessary, as well as the compound (II). In general, the carbon sources which are employable include, for example, glucose, sucrose, molasses, starch, dextrin, glycerin and sorbital. Operable as the nitrogen sources are, for example, organic nitrogen sources such as meat extract, soybean meal, corn steep liquor, casein, peptone and cotton seed meal as well as inorganic salts such as ammonium salts and nitrates, and these are utilized solely or in combination.

Examples of the compound (II) which is usable include the compound of the formula (II) wherein R is H, or cytosine, or cytidine, cytidylic acid, etc. which decomposes in the culture medium to produce cytosine, as well as nucleic acids or their hydrolyzates, or microorganism cells and agricultural, livestock and marine resources containing large amounts thereof; also employed is the compound wherein R is a halogen atom, or 5-halogenocytosine, or compound which decomposes in the culture medium to produce 5-halogenocytosine, such as 5-halogenocytidine and 5-halogenocytidylic acid; further utilizable is the compound where R is an alkyl group, or 5-alkylcytosine, or compound which decomposes in the culture medium to produce 5-alkylcytosine, such as 5-alkylcytidine and 5-alkylcytidylic acid, as well as 5-hydroxymethylcytosine or a compound which produces it in the culture medium. The addition concentration, to which the compound (II) is added or compound producing the compound (II) in the culture medium is added, is desirably in the range of 0.01 to 1.0% (weight/volume) as the compound (II), and further desirably in the range of 0.03 to 0.5% (weight/volume). The time at which the compound (II) is added to the culture medium is most effectively before the cultivation is initiated, although the addition during the cultivation at an appropriate time may be justifiable.

In order to ameliorate the production of the compound (III), furthermore, it is preferred to allow an N-methyl compound to exist in the culture medium. Such N-methyl compound includes compounds having not less than one nitrogen atom substituted with 1 to 4 methyl groups. Preferred among others are, for example, compounds having one nitrogen atom substituted with methyl groups, and in particular, quarternary ammonium salts having trimethylammonio group in which the nitrogen is substituted with three methyl groups, i.e., $-N^+(CH_3)_3$, are suited. Further, compounds having a group capable of being converted into a $>N-CH_3$ in the culture medium, for example, N,N-methylenebisacrylamide, can also be used as the N-methyl compound. The N-methyl compounds generally have molecular weights of 50 to 1000, preferably 90 to 130. The N-methyl compounds may be water-soluble or water-insoluble, but water-soluble N-methyl compounds can be used advantageously. Specific examples of such N-methyl compounds which are operable include N-methyl acid amides, N-methylamino compounds, N-methylamines, N-methylammonium compounds, polymethylenediamines, N,N-methylenebisacrylamide, etc. The N-methyl acid amides such as N,N-dimethyl $C_{2-6}$ aliphatic acid amides (e.g. N,N-dimethylacetamide, etc.), N-methylalkenylcarbonylamides (e.g. N-methylacrylamide, etc.) and the like, the N-methylamino compounds such as mono, di, tri or tetramethylureas (e.g. N-methylurea, 1,1,3,3-tetramethylurea, etc.), dimethylaminoalcohols (e.g. 2-dimethylaminoethanol, etc.) and the like, the N-methylamines such as mono, di or trimethylamines (e.g. trimethylamine, dimethylamine, etc.), and the like, the N-methylammonium compounds such as phosphatidylethanol-mono, di or trimethylammoniums (e.g. lecithin, etc.), trimethylammonium alcohols (e.g. choline, etc.), trimethylammonium carboxylic acids, (e.g. betaine, etc.), alkyltrimethylammoniums (e.g. tetramethylammonium, etc.), ethylenebis (trimethylammonium(chloride and the like, and polymethylenediamines such as ethylenediamine, tetramethylenediamine, hexamethylenediamine and the like are used advantageously. The use of N-methylammonium compounds, particularly choline, betaine and tetramethylammonium produces a satisfactory result. These N-methyl compounds can be used solely or as a mixture of two or more species. The present invention also includes, within the scope thereof, a method comprising adding a large amount of an N-methyl compound-containing substance such as beet molasses containing betaine, soybean meal containing lecithin or hen's egg containing both choline and lecithin to a culture medium so as to provide more than 3 mM of N-methyl compounds to the medium. The concentration of N-methyl compounds in the culture medium can be suitably selected from within the range which does not inhibit growth of the microorganism used, and is normally in the region of not less than 3 mM. The addition in the range of preferably 4 mM to 200 mM, more preferably 7 to 50 mM, is effective, and the addition in excess of 200 mM lowers an increase in the effect achieved by the addition. The addition amount of naturally occurring substances containing N-methyl compounds can be selected so as to provide the N-methyl compound concentration as specified above, but such concentration would require a larger amount of naturally occurring substances than that conventionally used whereby the growth of the microorganism may be adversely affected by components of the naturally occurring substances other than N-methyl compounds thereby preventing the production of mildiomycin. In such cases, it is preferred to use N-methyl compounds in combination with the naturally occurring substances. The time at which these N-methyl compounds are incorporated in the culture medium is before the culture medium is inoculated with the microorganism in view of ease in operation and effectiveness, but N-methyl compound can also be added at an appropriate time during the cultivation.

Cultivation can be conducted by the surface culture, but normally submerged aerobic culture is reasonable. In the case of the submerged aerobic culture, the solution of the culture medium is preferably kept slightly acidic or slightly alkaline, and the cultivation temperature is desirably maintained at 15° to 40° C., particularly 24° to 34° C. However, needless to say, such conditions of cultivation should be suitably selected depending upon the species of the strain used, environmental conditions, etc. so as to produce the favorable results. When the cultivation is continued for 4 days to 14 days, normally, there results a culture broth containing a considerable amount of the compound (III), and in order to recover the compound (III) from such culture broth, the separation and recovery procedures which are normally utilized for the recovery of metabolites by microorganisms from their culture broths can be suitably employed. For example, since the compound (III) is a water-soluble, basic substance and contained primarily in the culture broth, the microbial cells and other insoluble matter are in the first place removed by a procedure such as filtration and centrifugation; the resultant filtrate or supernatant is contacted with a suitable adsorbent such as activated carbon, adsorptive resins, cation exchange resins, activated alumina, silica gel or adsorbents, e.g. molecular sieve to adsorb the objective substance, and then, the objective substance can be eluted with an aqueous solution of a water-soluble organic solvent such as acetone, methanol, ethanol, propanol and butanol, or an acid, an alkali, a buffer or an aqueous solution of an inorganic or organic salt being used as a solvent; and, after conducting into practice an appropriate combination of these separation procedures, the effective fraction is concentrated and powdered, whereby the compound (III) can be recovered in the free state or in the form of a salt.

Meanwhile, the compound (II) being employed as a starting material can be produced by the procedures as described for example in Journal of the American Chemical Society, vol. 56, pp. 134 to 139 and Journal of Labelled Compounds, vol. 9, No. 3, pp. 475 to 482, or equivalent procedures.

The fungicidal and acaricidal agent for plants according to the present invention is incorporated with the compound (I) as an active ingredient.

The compound (I) may be utilized solely or in coexistence with other chemicals being applicable to plants.

With regard to forms of preparations, various forms of preparations for known fungicidal agents for plants can be adopted. For example, by dissolving or dispersing in a liquid carrier (for example, a solvent), or mixing or adsorbing with a suitable solid carrier (for example, diluent and dust diluent) and adding, as required, to these an emulsifying agent, dispersing agent, suspending agent, spreader, penetrant, wetting agent, sticking agent, stabilizer, etc., the compound (I) is used in the forms of preparations such as oil solution, emulsifiable concentrate, wettable powder, dust, tablets, granules and spraying agent.

The concentration of the major active ingredient (I) is suitably in the range of 1 to 70% for the emulsifiable concentrate, wettable powder, etc., and in the range of 0.01 to 10% for the oil solution, dust, etc., although such concentrations may be suitably changed depending upon the application purposes. In the meanwhile, the emulsifiable concentrate, wettable powder, etc. may be sprayed by diluting and extending suitably (for example, up to 100 to 10000 times) with water, etc. on the occasion of their use.

Suitable examples of the solvent which is used for the fungicidal and acaricidal agent for plants according to the present invention include water, alcohols (e.g., methyl alcohol, ethyl alcohol, ethylene glycol, etc.), ethers (e.g., dioxane, tetrahydrofurane, cellosolve, etc.), aliphatic hydrocarbons (e.g., gasoline, kerosene, light oil, fuel oil, machine oil, etc.), aromatic hydrocarbons (e.g., benzene, toluene, xylene, solvent naphtha, methylnaphthalene, etc.) and other organic bases (e.g., pyridine, aldehyde collidine, etc.), halogenated hydrocarbons (e.g., chloroform, carbon tetrachloride, etc.), acid amides (e.g., dimethylformamide), esters (e.g., ethyl acetate, butyl acetate, glycerin esters of fatty acids, etc.), nitriles (e.g, acetonitrile), and other solvents, and these are used solely or as a mixture of two or more species thereof.

The diluent and dust diluene include powders of plant origin (e.g., soybean meal, tobacco meal, flour, wood meal, etc.), powders of mineral origin (e.g., clays such as kaolin, bentonite and acid clay, talcs such as talc powder and pyrophyllite powder, silicas such as diatomaceous earth and mica powder, etc.), alumina, sulfur powder, activated carbon and the like, and these are used alone or as a mixture of two or more species thereof.

Examples of the surfactants which can be extensively employed for the emulsifier, spreader, penetrant, dispersing agent and the like include soaps, sulfuric acid esters of higher alcohols, alkylsulfonic acids, alkylarylsulfonic acids, quaternary ammonium salts, oxyalkylamines, fatty acid esters, polyalkylene oxide based surfactants, anhydrosorbitol based surfactants and so on. In addition, casein, gelatin, starch, alginic acid, agar, polyvinyl alcohols, wood terpentine oil, rice bran oil, bentonite, cresol soap, etc. may be employed as required.

Other than the compound (I), different types of fungicides (e.g., copper based fungicides, mercurial fungicides, organic sulfur fungicides, phenol based fungicides, etc.), herbicides, insecticides (organic chlorine insecticides, organophosphorus insecticides, natural insecticides, etc.), other miticides, nematocides, plant growth regulators, synergists, attractants, repellents, perfumes, plant nutrients, fertilizers and so on can be compounded and used as a mixture.

The application amount of the fungicidal and acaricidal agent for plants according to the present invention or the proper combination thereof with other types of chemicals to be mixed and the formulation ratios for them, for example, vary depending upon the variety of crop plants to which the fungicidal and acaricidal agent is to be applied, the growth stage and conditions of the crop plant, the method of growing the plant, the type of disease, the condition of onset, the time at which the agent is applied, the condition of surroundings, the methods and economics of application and other conditions. Usually, however, it is sufficient to apply at the rate of about 1 to 300 g per 10 areas. As regards the application concentration, the final concentration of the compound (I) of the present invention contained is suitably in the range of 1 $\mu$g/ml to 10 mg/ml. As to the application method, the fungicidal and acaricidal agent of the present invention may be scattered directly to the surface of crop plants or injected in the soil.

In other words, the present invention is not limited in whatever manner by the amount, concentration and method of application, but all that is necessary is to ensure that the fungicidal and acaricidal agent will be applied safely and effectively to crop plants.

The fungicidal and acaricidal agent for plants according to the present invention is useful in that it is effective against various diseases of plants and exhibits in addition the miticidal activity. The fungicidal and acaricidal agent is particularly effective against powdery mildew of edible crop (e.g., barley), industrial crop (e.g., tabacco), fruit trees (e.g., apple), forest crop (e.g., oak or *Quercus glauca*), vegetables (e.g., cucumber, oriental melon, green pepper and tomato), ornamental plants (e.g., rose) and so on, as well as against diseases of tomato, potato and other plants. Further, the fungicidal and acaricidal agent is substantially nontoxic (e.g., in terms of acute toxicity, irritant action to the eye mucosa and the skin, fish toxicity, etc.), and is extremely safe to use.

The present invention is further illustrated in greater detail by the following Examples and Test Examples, it being understood that these examples are not to be construed as limiting the present invention. In this specification, the following abbreviations are used: Liter=l, milliliter=ml, microliter=$\mu$l, kilogram=Kg, gram=g, milligram=mg, microgram=$\mu$g, centimeter=cm, millimeter=mm, nonameter=nm, percent (weight/volume)=%, rotation per minutes=r.p.m., Inner Diameter=ID, decomposition=decomp. and temperature=temp. The numbers indicated by IFO, FERM-P and ATCC are the accession numbers at Institute for Fermentation, OSAKA, JAPAN; the Fermentation Research Institute of the Agent of Industrial Science and Technology, Chiba, JAPAN, and American Type Culture Collection, U.S.A., respectively.

EXAMPLE 1

In a Sakaguchi flask with a 2 l capacity was distributed 500 ml of a culture medium composed of 1% of glucose, 0.3% of yeast extract and 0.5% (weight/volume) of peptone, after being adjusted to pH 7 with a 20% aqueous solution of caustic soda, and then sterilized. The flask was inoculated with *Streptoverticillium rimofaciens* IFO 13592 (FERM-P 2549, ATCC 31120) from a slant culture and incubated on a reciprocating shaker at 28° C. for 48 hours. In a fermentation tank with a 50 l capacity was charged 30 l of a culture medium composed of 10% of glucose, 1% of Proflo (produced by Trader Oil Mill Co.), 1% of corn steep liquor, 0.5% of sodium chloride, 0.5% of calcium carbonate, 0.001% of ferrous sulfate and 0.05% (weight/volume) of an antifoaming agent (Actocol, manufactured by Takeda Chemical Industries, Ltd., JAPAN), then adjusting to pH 7 with a 20% aqueous solution of caustic soda and sterilized to inoculate with 500 ml of the previously obtained culture from the Sakaguchi flask. Then, cultivation was carried out with aeration at 1 VVM (aeration volume per minute per unit volume of a fluid) under agitation at 100 r.p.m. at 28° C. for 48 hours to obtain a seed culture. In a fermentation tank with a capacity of 200 l, 100 l of the above seed medium supplemented with 100 g of cytosine was prepared and sterilized to transplant 10 l of the above seed culture. Cultivation was carried out with aeration at 0.5 VVM under agitation at 200 r.p.m. at 28° C. for 5 days.

30 l of the culture broth thus obtained was taken out, and 20 l of water and 1 kg of Hyflo-supercel (manufactured by Johnes-manville) were added to conduct filtration. 45 l of the resultant filtrate was passed through a column packed with 6 l of activated carbon for chromatographic uses (manufactured by Takeda Chemical Industries, Ltd.). After washing the column with 20 l of water, elution was performed with the use of 30 l of a 7% aqueous butanol solution, and the active fractions collected were passed through a column packed with 6 l of an ion exchange resin, Amberlite CG-50, H$^+$ type (manufactured by Rohm & Haas Company), followed by washing the column with 20 l of water to elute with a 2% aqueous ammonia. The active fractions were collected and concentrated under reduced pressure, and there was obtained 0.4 l of the concentrate, from which insolubles contained were filtered off. The filtrate was added dropwise to 3.5 l of ethanol, and the resultant precipitate was collected and dried, thus resulting in 15 g of a crude powder of the compound (I) wherein R is H.

EXAMPLE 2

In 30 ml of water was dissolved 5 g of the crude powder of the compound as obtained in Example 1, and the solution was passed through a column packed with 1 l of an ion exchange resin, Amberlite CG-50 (manufactured by Rohm & Haas Company) and buffered with a 0.3 M lithium borate buffer (pH 8.8), followed by eluting with the same buffer to separate out the active fractions. The resultant active fractions were passed through a column packed with 50 ml of activated carbon for chromatographic uses (manufactured by Takeda Chemical Industries, Ltd.) to be adsorbed, and after washing the column with 200 ml of water, elution was performed with a 5% aqueous butanol solution. The active fractions were collected and concentrated under reduced pressure, and the concentrate was added dropwise to ethanol to separate out the precipitate. The precipitate was collected and dried, thereby yielding 1.2 g of the compound (I) wherein R is H.

EXAMPLE 3

In water was dissolved 4 g of the crude powder of the compound as obtained in Example 1, and the solution was chromatographed on a column packed with 1.8 l of an ion exchange resin, Amberlite CG-50, in the same manner as in Example 2 to collect the active fractions. The fractions were passed through a column of 40 ml of activated carbon for chromatographic uses to be adsorbed, and after washing the column with 150 ml of water, elution was effected with a 20% aqueous acetone solution containing 0.5% of formic acid (all on a weight/volume basis). The collected active fractions are concentrated under reduced pressure and added dropwise to ethanol. The precipitate separated out was collected and dried, thereby yielding 1.0 g of formate of the compound (I) wherein R is H. Its typical physico-chemical properties are as follows.

Melting point: 227° C. (decomp.)

Optical rotation: $[\alpha]_D^{22} = +71.3°$ (c=0.5, water)

Absorption in the ultraviolet: $\lambda_{max}^{H2O} = 268$ nm, $E_{1\,cm}^{1\%} = 163$ Elementary analysis: C=39.12%, H=6.47%, N=18.93%

EXAMPLE 4

When cytosine was added to the culture medium at various concentrations as indicated in Table 1 shown below in conducting the cultivation by the procedure of Example 1, there was obtained the compound (I) wherein R is H in the amounts as indicated in Table 1.

TABLE 1

| Relationship between the added amounts of cytosine and the produced amounts of the compound with R = H. ||
|---|---|
| Added concentration of cytosine, % | Produced amount of the compound (I) with R = H, µg/ml |
| 0 | 0 |
| 0.01 | 250 |
| 0.05 | 1050 |
| 0.1 | 1650 |
| 0.2 | 1200 |
| 0.5 | 600 |
| 1.0 | 50 |

EXAMPLE 5

The cultivation in a tank was conducted with *Streptoverticillium rimofaciens* IFO 13592 (FERM-P 2549, ATCC 31120) used as the seed microorganism in the same manner as described in Example 1, except that 100 g of 5-bromocytosine was added to a fermentation tank with a 200-l capacity in place of cytosine.

Under the same conditions as described in Example 1, the cultivation was conducted with the use of a fermentation tank with a 200-l capacity to obtain about 100 l of the culture broth. 30 l of the culture broth thus obtained was taken out, and 20 l of water and 1 kg of Hyflosupercel (manfactured by Johnes-Manville) were added to the broth to effect filtration. 45 l of the resultant filtrate was passed through a column packed with 6 l of activated carbon for chromatographic uses (manufactured by Takeda Chemical Industries, Ltd.). After washing the column with 20 l of water, elution was performed using 30 l of a 7% aqueous isobutanol solution to collect the active fractions. The active fractions were passed through a column of 6 l of an ion exchange resin, Amberlite IRC-50 (manufactured by Rohm & Haas Company) H$^+$ type, and after washing the column with 20 l of water, elution was performed with a 2% aqueous ammonia. The active fractions after the elution were collected and concentrated under reduced pressure, there was obtained 0.4 l of the concentrate, from which insolubles were filtered off. The filtrate was added dropwise to 3.5 l of ethanol, and the resultant precipitate was collected and dried, thereby yielding 10.5 g of crude powder. 5 g of the crude powder was re-purified in the same manner as described in Example 2, resulting in 1.8 g of the compound (I) with R=Br.

EXAMPLE 6

The cultivation in a tank was conducted with *Streptoverticillium rimofaciens* IFO 13592 (FERM-P 2549, ATCC 31120) used as the seed microorganism in the same manner as described in Example 1, except that 100 g of 5-methylcytosine was added in this Example in place of cytosine in Example 1.

Under the same conditions as described in Example 1, the cultivation was conducted with the use of a fermentation tank with a 200-l capacity to obtain about 100 l of the culture broth. 30 l of the culture broth thus obtained was taken out, and the same purification procedure as the purification method in Example 5 was conducted, thereby yielding 1.5 g of the powder of the compound (I) with R=$CH_3$.

EXAMPLE 7

The cultivation in a tank conducted with *Streptoverticillium rimofaciens* IFO 13592 (FERM-P 2549, ATCC 31120) used as the seed microorganism in the same manner as described in Example 1, except that 100 g of 5-fluorocytosine was added in this Example in place of cytosine added in Example 1.

Under the same conditions as described in Example 1, the cultivation was conducted with the use of a fermentation tank with a 200-l capacity to obtain about 100 l of the culture broth. Thirty liter of the culture broth thus obtained was taken out, and the same purification procedure as the purification method indicated in Example 5 was conducted, thereby yielding 1.6 g of the powder of the compound (I) with R=F.

The compounds (I) of a free base type as obtained in the above Examples 2, 5, 6 and 7 showed the following properties.

(1) Solubilities:
Easily soluble in water but less soluble in organic solvents.

(2) Color reactions:
Sakaguchi reaction and potassium permanganate; positive, aniline phthalate reaction and ninhydrin reaction; pseudopositive, and Ehrlich reaction, Dragendorff reaction and Barton reaction; negative.

(3) Thin-layer chromatography:

Rf values in thin-layer chromatography of the compounds as obtained in Examples 2, 5, 6 and 7 are summarized in Table 2.

TABLE 2

| | | Rf values in thin-layer chromatography | | | |
|---|---|---|---|---|---|
| | | Rf value | | | |
| Carrier | Solvent* | Compound of Example 2 | Compound of Example 5 | Compound of Example 6 | Compound of Example 7 |
| Silica gel | Solvent 1 | 0.048 | 0.068 | 0.055 | 0.05 |
| | Solvent 2 | 0.03 | 0.08 | 0.05 | 0.06 |
| | Solvent 3 | 0.11 | 0.16 | 0.14 | 0.14 |
| | Solvent 4 | 0.08 | 0.17 | 0.14 | 0.14 |
| Cellulose | Solvent 1 | 0.87 | 0.90 | 0.87 | 0.90 |
| | Solvent 2 | 0.30 | 0.40 | 0.46 | 0.45 |
| | Solvent 3 | 0.17 | 0.25 | 0.27 | 0.20 |
| | Solvent 4 | 0.22 | 0.33 | 0.28 | 0.25 |

Remarks,
*The Solvents 1 through 4 designate the following mixed solvents, respectively.
Solvent 1 n-Propanol : water (3:7)
Solvent 2 Methanol : water (4:6)
Solvent 3 Upper layer of chloroform : methanol : 17% aqueous ammonia (2:2:1)
Solvent 4 n-Propanol : pyridine : glacial Acetic acid : water (15:10:3:10)

(4) Melting points:
Each of the compounds undergoes gradual carbonization at a temperature in the region of 230° C., and does not show any clear melting point.

(5) Specific rotations:
Specific rotations are summarized in Table 3.

TABLE 3

| Specific rotations | |
|---|---|
| Compound | $[\alpha]_D^{20}$ (c = 0.5, water) |
| Compound of Example 2 | +79.5° |
| Compound of Example 5 | +114.6° |
| Compound of Example 6 | +88.5° |
| Compound of Example 7 | +77.0° |

(6) Elementary analysis
Elementary analysis is summarized in Table 4, wherein values of Elementary analysis for each of the compounds as shown indicate that the found values are substantially in accordance with the calculated ones.

TABLE 4

| | Elementary analysis | | | |
|---|---|---|---|---|
| | Compound of Example 2 | Compound of Example 5 | Compound of Example 6 | Compound of Example 7 |
| Molecular formula | $C_{18}H_{28}O_8N_8 \cdot 3H_2O$ | $C_{18}H_{27}O_8N_8Br \cdot 2H_2O$ | $C_{19}H_{30}O_8N_8 \cdot 2H_2O$ | $C_{18}H_{27}O_8N_8F \cdot 3H_2O$ |
| Molecular weight | 538 | 599 | 534 | 556 |
| Calcd. (%) | | | | |
| C | 40.1 | 36.1 | 42.7 | 38.8 |
| H | 6.3 | 5.2 | 6.4 | 5.9 |
| O | 32.8 | 26.7 | 30.0 | 31.7 |
| N | 20.8 | 18.7 | 21.0 | 20.1 |
| Br | — | 13.4 | — | — |
| F | — | — | — | 3.4 |
| Found (%) | | | | |
| C | 40.3 | 35.8 | 42.5 | 39.0 |
| H | 6.4 | 5.3 | 6.5 | 5.5 |
| O | 32.9 | 27.2 | 29.6 | 32.3 |
| N | 20.4 | 18.3 | 21.4 | 20.2 |
| Br | — | 13.4 | — | — |
| F | — | — | — | 3.0 |

(7) Ultraviolet absorption spectra:
The spectra were obtained using water, 1/10 N NaOH and 1/10 N HCl as a solvent, respectively, and their maxima, $\lambda_{max}$, and $E_1\ cm^{1\%}$ in the case of water used as a solvent are summarized in Table 5.

TABLE 5

| | Absorption maxima in the ultraviolet and $E_{1cm}^{1\%}$ | | | |
|---|---|---|---|---|
| | Maximum $\lambda_{max}$ (nm) | | | |
| | $H_2O$ | $1/10$N NaOH | $1/10$N HCl | $E_{1cm}^{1\%}(M_2O)$ |
| Compound of Example 2 | 268 | 268 | 276 | 175.0 |
| Compound of Example 5 | 286 | 286 | 296 | 117.6 |
| Compound of Example 6 | 275 | 276 | 284 | 168.7 |
| Compound of Example 7 | 277 | 276 | 284 | 153.5 |

(8) Nuclear magnetic resonance spectra:

Indicated in Table 6 and δ values (ppm) obtained from the $^{13}$C-NMR spectra measured in heavy water.

TABLE 6

| | $^{13}$C—NMR spectra, δ values (ppm) | | | | |
|---|---|---|---|---|---|
| Carbon number | Compound of Example 2 | Compound of Example 5 | Compound of Example 6 | Compound of Example 7 | |
| 2 | 158.0 | 156.8 | 158.0 | 156.3 | |
| 4 | 166.7 | 163.4 | 166.7 | 159.0 | ($J_{CCF}$ = 15Hz) |
| 5 | 97.4 | 90.1 | 105.5 | 138.1 | ($J_{CF}$ = 244.6Hz) |
| 6 | 143.4 | 143.9 | 140.4 | 127.4 | ($J_{CCF}$ = 31.9Hz) |
| 7 | — | — | 13.1 | — | |
| 1' | 80.9 | 81.0 | 80.9 | 80.9 | |
| 2' | 126.8 | 126.4 | 127.0 | 126.5 | |
| 3' | 133.9 | 134.2 | 133.7 | 134.2 | |
| 4' | 44.0 | 43.9 | 44.0 | 43.9 | |
| 5' | 80.6 | 80.9 | 80.6 | 80.9 | |
| 6' | 79.4 | 79.5 | 79.4 | 79.5 | |
| 7' | 39.3 | 39.1 | 39.2 | 39.1 | |
| 8' | 67.8 | 67.8 | 67.9 | 67.8 | |
| 9' | 48.1 | 48.1 | 48.1 | 48.1 | |
| 10' | 158.0 | 157.9 | 158.0 | 158.0 | |
| 11' | 178.8 | 178.9 | 178.7 | 178.9 | |
| 1" | 174.9 | 174.9 | 174.9 | 174.4 | |
| 2" | 57.0 | 57.0 | 57.1 | 56.9 | |
| 3" | 64.4 | 64.4 | 64.4 | 64.1 | |

(9) High-speed liquid chromatography:

The compounds were chromatographed on a column of 2.1 mm ID×450 mm packed with Hitachi ion exchange resin #2610 with the mobile phase of 0.3 M lithium borate buffer (pH 9.02) at a temperature of 45° C., at a pressure of 90 to 110 kg/cm$^2$ and at a flow rate of 0.6 ml/min. to detect the absorptions at 254 nm, whereby the retention time was found to be 9.5 minutes for the compound of Example 2, 12.5 minutes for the compound of Example 5, 10.5 minutes for the compound of Example 6 and 5.8 minutes for the compound of Example 7.

(10) Biological activities:

The antimicrobial spectrum of the compound (I) as measured by the agar dilution method (in vitro) is as shown in Table 7. Thus, it is obvious that the compound (I) shows the antimicrobial activity against certain types of bacteria and plant pathogenic fungi as well as some yeasts. Particularly, the compound of Example 5 exhibited the remarkably strong antimicrobial activity against some bacteria.

TABLE 7

| | Antimicrobial spectrum | | | | | | |
|---|---|---|---|---|---|---|---|
| | Conditions of assay | | | Minimal inhibitory concentration (μg/ml) | | | |
| Assay organism | Medium | Temp. (°C.) | Time (hr) | Compound of Example 2 | Compound of Example 5 | Compound of Example 6 | Compound of Example 7 |
| Penicillium chrysogenum IFO 4626 | A | 28 | 40 | 250 | 250 | 250 | 250 |
| Cochlioborus miyabeanus IFO 5277 | A | 28 | 40 | 100 | 100 | 100 | 100 |
| Sclerotinia sclerotiorum IFO 9395 | A | 28 | 40 | 250 | 500 | 250 | 250 |
| Guignardia laricina IFO 7886 | A | 28 | 88 | 250 | 250 | 250 | 250 |
| Saccharomyces cerevisiae IFO 0209 | A | 28 | 40 | 100 | 100 | 100 | 100 |
| Rhodotorula rubra IFO 0870 | A | 28 | 40 | <10 | <10 | <10 | <10 |
| Bacillus subtilis IFO 3513 | B | 37 | 20 | 250 | 250 | 250 | 250 |
| Escherichia coli IFO 12734 | B | 37 | 20 | 250 | 100 | 250 | 250 |

TABLE 7-continued

| | Conditions of assay | | | Antimicrobial spectrum Minimal inhibitory concentration (μg/ml) | | | |
|---|---|---|---|---|---|---|---|
| Assay organism | Medium | Temp. (°C.) | Time (hr) | Compound of Example 2 | Compound of Example 5 | Compound of Example 6 | Compound of Example 7 |
| *Proteus vulgaris* IFO 3045 | B | 37 | 20 | >500 | 250 | >500 | >500 |
| *Mycobacterium phlei* IFO 3158 | C | 37 | 40 | 50 | 25 | 50 | 25 |
| *Mycobacterium smegmatis* ATCC 607 | C | 37 | 40 | 100 | 25 | 100 | 100 |

Assay media
A 3.0% of sucrose, 0.2% of L-asparagine, 0.3% of $NH_4NO_3$, 0.1% of $KH_2PO_4$, 0.1% of $MgSO_4 \cdot 7H_2O$, 0.001% of versenol (manufactured by Dow Chemical Co.; an iron chelate compound, content of iron sodium ethanol ethylene diamine triacetate is 57.04%) and 1.5% of powder agar (pH 7).
Before use, the following vitamins are added to the medium to the indicated final concentrations: 1 μg/ml. thiamine, 1 μg/ml. riboflavin, 1 μg/ml. calcium pantothenate, 1 μg/ml. niacin, 0.005 μg/ml. biotin, 0.5 μg/ml. folic acid, 2 μg/ml. pyridoxine hydrochloride, 0.5 μg/ml. p-aminobenzoic acid, 0.0002 μg/ml. cyanocobalamin.
B 0.5% of Ehrlich's meat extract, 0.5% of polypeptone, 0.5% of NaCl, 1.5% of powder agar (pH 7).
C 3.0% of glycerin, 0.5% of Ehrlich's meat extract, 0.5% of NaCl, 1.5% of powder agar (pH 7.0).

(11) Toxicity:
The acute toxicities in mice of the compounds of Examples 2, 5, 6 and 7 are as follows:

| $LD_{50}$ (mg/kg); | Intravenous injection, | >100 |
|---|---|---|
| | Intraperitoneal administration, | >200 |
| | Subcutaneous injection, | >200 |

EXAMPLE 8

In the same manner as described in Example 1, the medium was inoculated with *Streptoverticillium rimofaciens* IFO 13592 (FERM-P 2549, ATCC 31120) to obtain the seed culture broth. To the basic culture medium comprising 10% of glucose, 3% of cotton seed germ flour (trade name, "Proflo", Trader Oil Mill Co.), 1% of corn steep liquor, 0.5% of sodium chloride, 0.5% of calcium carbonate, 0.001% of ferrous sulfate and 0.05% (weight/volume) of an antifoaming agent (trade name, "Actcol", manufactured by Takeda Chemical Industries, Ltd.) were various additives as being described below. After adjusting to pH 7 with 20% aqueous caustic soda solution, the culture medium was distributed in 25 ml quantities into Erlenmeyer flasks with a 200-ml capacity. As being indicated in Table 8, five kinds of the compounds corresponding to the compounds (II) wherein R' is H, Br, $CH_3$, I and F, respectively, were each added to the separate flasks. Each of the culture media was then divided into the two equal portions to add, and not to add, choline as an N-methyl compound. In this way, there were prepared eight kinds of the culture media in total. 1 ml of the seed culture broth was transferred to each of eight kinds of the culture media to cultivate on a rotary shaker (speed of revolution of 200 r.p.m.) at 28° C. for 5 days. The culture broth was centrifuged with the condition of 5000 g to remove microbial cells, and the resultant supernatant was diluted to 50 times to subject to high-speed liquid chromatography. The products in the culture broths, the compound (III) (R'=H) in the case of addition of the compound (II) with R'=H, the compound (III) (R'=Br) in the case of addition of the compound (II) with R'=Br, the compound (III) (R'=$CH_3$) in the case of addition of the compound (II) with R'=$CH_3$, the compound (III) (R'=I) in the case of addition of the compound (II) with R'=I, and the compound (III) (R'=F) in the case of addition of the compound (II) with R'=F were quantitatively determined according to the procedure described in the following.

A cation exchange resin, Hitachi 2610, was packed into a 45-cm long column, which was fitted in the high-speed liquid chromatograph (manufactured by Waters Co., type 6000 A) and a 0.3 M boric acid-lithium hydroxide buffer (pH 9.02) was allowed to flow through at a rate of 0.6 ml/min., while warming the column at 45° C. When 25 μl of the diluted culture broth was poured into the column, flown through it were the compound (III) (R'=H) with the retention time of 9.5 minutes, the compound (III) (R'=Br) with 12.5 minutes, the compound (III) (R'=$CH_3$) with 10.5 minutes, the compound (III) (R'=I) with 20.5 minutes and the compound (III) (R'=F) with 5.8 minutes, respectively, whereby the UV detector provided the detection of ultraviolet absorptions at the wave-length of 254 nm and quantitative determination was made from maxima of the absorption curves recorded on the self-recording device.

TABLE 8

Effect of N-methyl compound (choline)

| Added compound (the compound (II)) (0.2% in the broth) | Choline added (0.1% of concentration in the broth) Not added | Accumulated amount of the product in the broth* (μg/ml) |
|---|---|---|
| R' = H | Added | 4,100 |
| | Not added | 2,000 |
| R' = Br | Added | 3,950 |
| | Not added | 2,100 |
| R' = $CH_3$ | Added | 4,100 |
| | Not added | 2,050 |
| R' = I | Added | 3,950 |
| | Not added | 2,010 |
| R' = F | Added | 4,150 |
| | Not added | 2,030 |

Remarks,
*Quantitatively determined by calculation based on the maximum at 254 nm of the ultraviolet absorption curve for the compound (III) which resulted from high-speed liquid chromatography.

Resin: Hitachi 2610 cation exchange resin, length of a column: 45 cm, temperature at which the column was warmed: 45° C., eluting solution: a 0.3 M boric acid-lithium hydroxide buffer (pH 9.02), flowing rate: 0.6 ml per minute.

The retention times of the products found in the high-speed liquid chromatography under the above conditions are as follows. The products are the compounds (III) (R'=H, Br, CH₃, I and F, respectively); R'=H, 9.5 minutes; R'=Br, 12.5 minutes; R'=CH₃, 10.5 minutes; R'=I, 20.5 minutes; R'=F, 5.8 minutes.

EXAMPLE 9

In the same manner as described in Example 8, except that trimethylamine was used as an N-methyl compound in place of choline, the effect produced by addition thereof was determined. The results are shown in Table 9.

TABLE 9
Effect of N-methyl compound (trimethylamine)

| Added compound (the compound (II)) (0.2% in the broth) | Trimethylamine added (0.1% in the broth) Not added | Accumulated amount of the product in the broth* ($\mu$g/ml) |
|---|---|---|
| R' = H | Added | 3,750 |
|  | Not added | 2,000 |
| R' = Br | Added | 3,610 |
|  | Not added | 2,100 |
| R' = CH₃ | Added | 3,970 |
|  | Not added | 2,050 |
| R' = I | Added | 3,680 |
|  | Not added | 2,010 |
| R' = F | Added | 3,740 |
|  | Not added | 2,025 |

Remarks,
*Quantitatively determined by calculation based on the maximum of the ultraviolet absorption curve for the compound (III) resulted from high-speed liquid chromatography.

The conditions are equivalent to those as described in Example 8.

EXAMPLE 10

In the same manner as described in Example 1, the culture medium was inoculated with *Streptoverticillium rimofaciens* IFO 13592 FERM-P 2549, ATCC 31120) to obtain the seed culture broth.

A culture medium composed of 10% of glucose, 3% of cotton seed germ flour (trade name, "Proflo", manufactured by Trader Oil Mill Co.), 1% of corn steep liquor, 0.5% of sodium chloride, 0.5% of calcium carbonate, 0.001% of ferrous sulfate and 0.05% (weight/volume) of an antifoaming agent (trade name, "Actcol", manufactured by Takeda Chemical Industries, Ltd.) was adjusted to pH 7 with a 20% aqueous caustic soda solution and distributed in 25 ml quantities into Erlenmeyer flasks to prepare the basic culture media. Using as an additive compound the compound (II) wherein R' is CH₂OH or 5-hydroxymethylcytosine, as indicated in Table 10, the comparative cultivation tests were conducted with and without addition of the compound. 1 ml of the seed culture broth was transferred and the cultivation was conducted on a rotary shaker (speed of revolution of 200 r.p.m.) at 28° C. for 5 days to determine quantitatively the product, the compound (III) wherein R' is CH₂OH or mildiomycin (which corresponds to the compound described in Tetrahedron Letters, No. 44, 4277–4280 (1978)) according to the same procedure as described in Example 9 by means of high-speed liquid chromatography. Mildiomycin was detected with the retention time of 5.6 minutes by high-speed liquid chromatography set under said conditions, and results of the quantitative determination are indicated in Table 10.

TABLE 10

| Effect of addition of 5-hydroxymethylcytosine | |
|---|---|
| 5-hydroxymethylcystosine added (0.2% (weight/volume) in the culture broth) | Accumulated amount of mildiomycin in the culture broth* ($\mu$g/ml) |
| Added | 2,380 |
| Not added | 840 |

Remarks
*Quantitatively determined by calculation based on the maximum of the ultraviolet (254 nm) absorption curve for mildiomycin which resulted from high-speed liquid chromatography. The conditions were equivalent to those as described in Example 8.

EXAMPLE 11

A wettable powder was obtained by mixing 10 parts of the compound of Example 2, 2 parts of sodium ligninsulfonate, 3 parts of polyoxyethylene alkylaryl ether and 85 parts of clay. The powder was diluted with water to 500 to 1000 times, and sprayed uniformly over farm or horticultural crop plants at a rate of 100 to 200 l per 10 ares.

EXAMPLE 12

A dust was obtained by mixing 0.5 part of the compound of Example 2 with 99.5 parts of clay. The dust was directly applied by dusting at a rate of 3 to 5 kg per 10 ares.

EXAMPLE 13

A water-soluble preparation was prepared by mixing 10 parts of the compound of Example 3, 5 parts of polyoxyethylene alkylaryl ether and 85 parts of lactose, with stirring. The preparation was diluted with water to the desired concentration and sprayed evenly over farm and horticultural crop plants at a rate of 100 l of 10 ares.

EXAMPLE 14

A water-soluble preparation obtained by mixing 50 parts of the compound of Example 5,5 parts of methanol, 5 parts of amine stearate and 40 parts of water was diluted with water and sprayed in the same way as described in Example 11.

EXAMPLE 15

A granule produced by mixing for granulation 0.5 part of the compound of Example 6, 5 parts of gum Arabic, 30 parts of bentonite and 64.5 parts of talc was directly applied at a rate of 3 to 5 kg per 10 ares.

TEST EXAMPLE 1

The control test of late blight of tomato was carried out. Tomato plants (*Lycopersicon esculentum* Mill, f. Ohgata Fukuju), which were grown in 12 cm-pots for 30 day days, were used in the test. The test was carried out in duplicate per group of 4 pots. The chemical solution was sprayed adequately and, two days later, a suspension of the planospores of fungi of late blight of tomato was directly sprayed over the plants. After the pots were kept in a greenhouse for 4 days, the percent area of the lesions (on the third and fourth leaves) was investigated. The results are shown in Table 11.

TABLE 11

| Concentration (ppm) | The effect against late blight of tomato Percent area of lesions (%)** | | | |
|---|---|---|---|---|
| | Compound of Example 2 | Compound of Example 5 | Compound of Example 6 | Compound of Example 7 |
| 150 | 55 | 100 | 100 | 100 |
| 200 | 0 | 11 | 17 | 16 |
| 250 | 0 | 0 | 0 | 0 |
| 300 | 0 | 0 | 0 | 0 |
| 500 | 0 | 0 | 0 | 0 |

Remarks,
**The non-treated group is taken as 100%.

TEST EXAMPLE 2

The controlling effect against powdery mildew of barley was investigated according to the method of Iwasa, et. al. (The Journal of Antibiotics, vol. 31, No. 6, pp. 512, 1978). The results indicate that all of the compounds of Examples 2, 5, 6 and 7 are greatly effective against it.

TEST EXAMPLE 3

The test on the miticidal effect was carried out. The seedlings (5 days after germination) of kidney bean grown in pots (9 cm in diameter) were inoculated on their main leaves with about 50 female adults of *Totranychus urticae*, and the test chemical solution was sprayed in 20 ml quantities per pot by means of a spray gun. After spraying, the pots were placed in a phytotron (28° C.), and a number of surving mites on leaves was investigated at the 5th and 7th day to determine a decrease rate against a number of mites immediately before spraying [=(number of mites tested-number of surving mites)/(number of mites tested)×100]. Table 12 indicates that all the compounds are remarkably effective. Investigation on the phytotoxicity against kidney bean conducted simultaneously shows that they all exhibit no phytocidal action.

TABLE 12

Effect of mildiomycin derivatives against *Totranychus urticae*

| Test compound | Concentration (ppm) | Decrease rate | |
|---|---|---|---|
| | | 5th day | 7th day |
| Compound of Example 2 | 500 | 100 | 100 |
| Compound of Example 5 | 500 | 100 | 100 |
| Compound of Example 6 | 500 | 100 | 100 |
| Compound of Example 7 | 500 | 100 | 100 |
| Not sprayed | — | 31.0 | −68.0* |

Remarks,
*Indicates an increase.

What we claim is:

1. A compound of the formula:

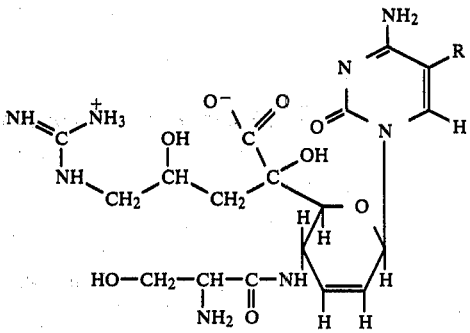

wherein R is hydrogen, a halogen atom or a lower alkyl group, or an acid salt thereof.

2. A compound as claimed in claim 1, wherein R is hydrogen.

3. A compound as claimed in claim 1, wherein R is a halogen atom.

4. A compound as claimed in claim 3, wherein the halogen atom is bromine, iodine or fluorine.

5. A compound as claimed in claim 1, wherein R is a lower alkyl group.

6. A compound as claimed in claim 5, wherein the lower alkyl group is a $C_{1-6}$ alkyl group.

7. A compound as claimed in claim 6, wherein the $C_{1-6}$ alkyl group is methyl group.

8. A process for producing a compound of the formula:

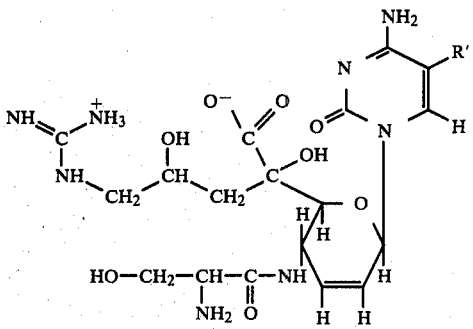

wherein R' is hydrogen, a halogen atom, a lower alkyl group or a hydroxymethyl group, or an acid salt thereof, which comprises cultivating a mildiomycin-microorganism belonging to the genus Streptoverticillium in a culture medium containing a compound of the formula:

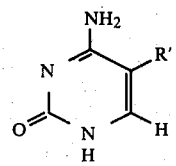

wherein R' has the same meaning as above, or an acid salt thereof to have said compound elaborated and accumulated in the culture broth.

9. A process according to claim 8, wherein the cultivation is performed in a culture medium containing not less than 3 mM of an N-methyl compound.

10. A plant fungicidal and acaricidal composition which comprises a fungicidally or acaricidally effective amount of a compound of the formula
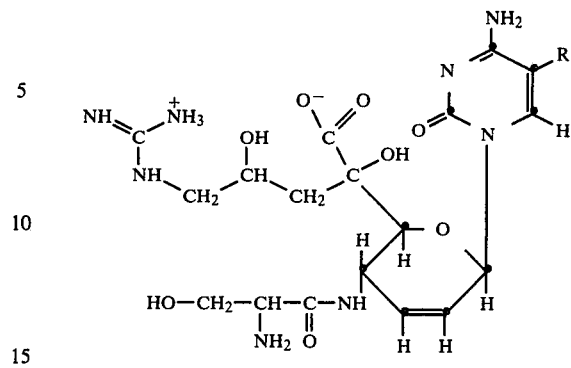
wherein R is hydrogen, a halogen atom or a lower alkyl group, or an acid salt thereof and a carrier therefor.
* * * * *